(12) United States Patent
Sebree et al.

(10) Patent No.: US 10,568,848 B2
(45) Date of Patent: *Feb. 25, 2020

(54) TREATMENT OF AUTISM WITH CANNABIDIOL

(71) Applicant: ZYNERBA PHARMACEUTICALS, INC., Devon, PA (US)

(72) Inventors: Terri Sebree, Gladwyne, PA (US); Marcel Bonn-Miller, Lexington, NC (US); Donna Gutterman, Raleigh, NC (US)

(73) Assignee: ZYNERBA PHARMACEUTICALS, INC., Devon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,248

(22) Filed: May 14, 2019

(65) Prior Publication Data

US 2019/0262280 A1    Aug. 29, 2019

Related U.S. Application Data

(63) Continuation of application No. 16/220,249, filed on Dec. 14, 2018, now Pat. No. 10,314,792, which is a continuation of application No. 16/144,632, filed on Sep. 27, 2018, now Pat. No. 10,213,390.

(60) Provisional application No. 62/632,532, filed on Feb. 20, 2018, provisional application No. 62/564,834, filed on Sep. 28, 2017.

(51) Int. Cl.
| | | |
|---|---|---|
| *A61K 36/00* | (2006.01) | |
| *A61K 31/05* | (2006.01) | |
| *A61K 36/185* | (2006.01) | |
| *A61P 25/00* | (2006.01) | |
| *A61K 9/00* | (2006.01) | |
| *A61K 9/06* | (2006.01) | |

(52) U.S. Cl.
CPC ............ *A61K 31/05* (2013.01); *A61K 9/0014* (2013.01); *A61K 9/06* (2013.01); *A61K 36/185* (2013.01); *A61P 25/00* (2018.01)

(58) Field of Classification Search
CPC ...................................................... A61K 36/00
USPC ......................................................... 424/725
See application file for complete search history.

(56) References Cited

U.S. PATENT DOCUMENTS

| | | |
|---|---|---|
| 8,293,786 B2 | 10/2012 | Stinchcomb et al. |
| 8,435,556 B2 | 5/2013 | Stinchcomb et al. |
| 8,449,908 B2 | 5/2013 | Stinchcomb et al. |
| 9,375,417 B2 | 6/2016 | Smith et al. |
| 9,447,019 B2 | 9/2016 | Mechoulam et al. |
| 9,533,942 B2 | 1/2017 | Stinchcomb et al. |
| 9,675,656 B2 | 6/2017 | Crowley |
| 9,730,911 B2 | 8/2017 | Verzura et al. |
| 9,782,360 B2 | 10/2017 | Mechoulam et al. |
| 2008/0139472 A1 | 6/2008 | Lauterborn et al. |
| 2010/0273895 A1 | 10/2010 | Stinchcomb et al. |
| 2011/0052694 A1 | 3/2011 | Stinchcomb et al. |
| 2015/0342902 A1 | 12/2015 | Vangara et al. |
| 2015/0343071 A1 | 12/2015 | Vangara et al. |
| 2016/0022627 A2 | 1/2016 | Smith |
| 2016/0256410 A1 | 9/2016 | Aung-Din |
| 2016/0256411 A1 | 9/2016 | Aung-Din |
| 2016/0271252 A1 | 9/2016 | Vangara et al. |
| 2016/0338974 A1 | 11/2016 | Aung-Din |
| 2017/0224634 A1 | 8/2017 | Vangara et al. |
| 2017/0274030 A1 | 9/2017 | Crowley |
| 2017/0360745 A1 | 12/2017 | Blackmon et al. |
| 2018/0140560 A1 | 5/2018 | De Vries et al. |

FOREIGN PATENT DOCUMENTS

| | | |
|---|---|---|
| WO | 2010/127033 A1 | 11/2010 |
| WO | 2016109624 A1 | 7/2016 |
| WO | 2017149387 A1 | 9/2017 |
| WO | 2017151980 A1 | 9/2017 |
| WO | 2017158539 A1 | 9/2017 |
| WO | 2017178807 A1 | 10/2017 |
| WO | 2017178810 A1 | 10/2017 |
| WO | 2017182950 A1 | 10/2017 |
| WO | 2018002637 A1 | 1/2018 |
| WO | 2018109471 A1 | 6/2018 |

OTHER PUBLICATIONS

Banks S, O'Neill C, Sebree T. Pharmacokinetic Evaluation of Subcutaneously Administered ZYN001 in Male Sprague-Dawley Rats. PAINWeek. Sep. 8-12, 2015.

Bergmaschi et al., Cannabidiol Reduces the Anxiety Induced by Simulated Public Speaking in Treatment-Naiver Social Phobia Patients, Neuropsychopharmacology (2011) 36, 1219-1226.

Blessing et al., Cannibidiol as a Potential Treatment for Anxiety Disorders, Neurotherapeutics, Oct. 2015, 12(4): 825-836.

Bonn-Miller M, Banks SL, Sebree T. Conversion of Cannabidiol Following Oral Administration: Authors' Response to Grotenhermen et al. Cannabis and Cannabinoid Research 2017;2:1, 5-7.

Bonn-Miller M, Gutterman D. A Permeation-Enhanced Synthetic Cannabidiol (CBD) Transdermal Gel for the Treatment of PTSD. Military Health System Research Symposium. Orlando, FL. Aug. 15-18, 2016.

(Continued)

*Primary Examiner* — Michael V Meller

(74) *Attorney, Agent, or Firm* — Womble Bond Dickinson (US) LLP; Danielle L. Herritt; Benedict Hanrahan

(57) ABSTRACT

The present technology relates to a method of treating one or more behavioral symptoms of Autism Spectrum Disorder (ASD) in a subject by transdermally administering an effective amount of cannabidiol (CBD) to the subject wherein one or more behavioral symptoms of ASD are treated in the subject.

8 Claims, No Drawings

(56) References Cited

OTHER PUBLICATIONS

Bonn-Miller M, Sebree T, O'Neill C, Messenheimer J. Neuropsychological Effects of ZYN002 (Synthetic Cannabidiol) Transdermal Gel in Healthy Subjects and Patients with Epilepsy: Phase 1, Randomized, Double-Blind, Placebo-Controlled Studies. American Epilepsy Society Annual Meeting. Houston, TX. Dec. 2-6, 2016.
Fusar-Poli, et al., "Modulation of Effective Connectivity During Emotional Processing by D9-tetrahydrocannabinol and Cannabidiol," International Journal of Neuropsychopharmacology (2010) 13, 421-432.
Gauvin D, O'Neill C, Patterson DR. Respiratory Evaluation of Subcutaneously Administered ZYN001 in Male Sprague-Dawley Rats. PAINWeek. Sep. 8-12, 2015.
Jung KM, Sepers M, et al. Uncoupling of the endocannabinoid signalling complex in a mouse model of fragile X syndrome. Nat Commun 2012;3:1080.
Kidd, et al., Cannabinoids in the Treatment of Autism Spectrum Disorder: Demanding Data Before Using Fad Therapies, Pediatric Neurology, 88 (2018) 10-11.
Lozano, et al., "Advances in the Understanding of Gabaeric Neurobiology of FMR1 Expanded Alleles Leading to Targeted Treatments for Fragile X Spectrum Disorder," Curr Pharm Des Author manuscript, (2015); 21 (34): 4972-4979.
Merrick J, Lane B, Sebree T, Yaksh T, O'Neill C, Banks SL. Identification of psychoactive degradants of cannabidiol in simulated gastric and physiological fluid. Cannabis and Cannabinoid Research 2016;1:1, 102-112, DOI: 10.1089/can.2015.0004.
Novagant Corp. Announces Breakthrough in Cannabidiol (CBD) Transdermal Patch for Localized Delivery, Oct. 29, 2014.
O'Brien T MD, FRACP; Berkovic, S, MD, FRACP; French, J, MD, et al. Synthetic Transdermal Cannabidiol for the Treatment of Focal Epilepsy in Adults. 2017 American Epilepsy Society Annual Meeting, Washington, DC. Dec. 1-5, 2017.
Paudel KS, Hammell DC, et al. Cannabidiol bioavailability after nasal and transdermal application: effect of permeation enhancers. Drug Development and Industrial Pharmacy 2010;36(9):1088-1097.
Qin M, Zeidler Z, et al. Endocannabinoid-mediated improvement on a test of aversive memory in a mouse model of fragile X syndrome. Behav Brain Res Sep. 15, 2015;291:164-71.
Salgado, et al., Autism Spectrum Disorder and Cannabidiol: Have We Seen This Movie Before?, Global Pediatric Health, vol. 5:1-5 (2018).
Sativex Product Monograph, Buccal Spray, Mar. 30, 2012 (55 pages).
Sebree T, O'Neill C, Messenheimer J, Gutterman D. Safety and Tolerability of ZYN002 (Synthetic Cannabidiol) Transdermal Permeation-Enhanced Gel in Healthy Subjects and Epilepsy Patients: Three Phase 1, Randomized, Double-Blind, Placebo-Controlled Studies. American Epilepsy Society Annual Meeting. Houston, TX. Dec. 2-6, 2016.
Wei, et al., Enhancement of Anandamide-Mediated Endocannabinoid Signally Corrects Autism-Related Social Impairment, Cannabis and Cannabinoid Research, vol. 1.1 (2016).
Wheeler, et al., "Anxiety, Attention Problems, Hyperactivity, and the Aberrant Behavior Checklist in Fragile X Syndrome," American Journal of Medical Genetics, (2013) 141-155.
Winton-Brown, et al., "Modulation of Auditory and Visual Processing by Delta-9-Tetrahydrocannabinol and Cannabidiol: an fMRI Study," Neuropsychopharmacology (2011) 36, 1340-1348.
Hadland, S., et al., "Medical Marijuana: Review of the Science and Implications for Developmental Behavioral Pediatric Practice," J Dev Behav Pediatr. 2015 ; 36(2): 115-123.
Aran, A., et al., "Cannabidiol Based Medical Cannabis in Children with Autism—a Retrospective Feasibility Study (P3.318)," Neurology, 90:15 Supplement, (2018).

TREATMENT OF AUTISM WITH CANNABIDIOL

CROSS REFERENCE TO RELATED APPLICATIONS

This application is a continuation of U.S. patent application Ser. No. 16/220,249 filed on Dec. 14, 2018, which is a continuation of U.S. patent application Ser. No. 16/144,632 filed on Sep. 27, 2018, which claims the benefit of and priority to U.S. provisional application No. 62/564,834 filed Sep. 28, 2017 and U.S. provisional application No. 62/632,532 filed Feb. 20, 2018. The contents of each of which are hereby incorporated herein in their entirety.

FIELD OF THE TECHNOLOGY

The present disclosure relates to methods of treating one or more behavioral symptoms of Fragile X Syndrome in a subject by transdermally administering an effective amount of cannabidiol (CBD) to the subject wherein one or more behavioral symptoms of Fragile X Syndrome are treated in the subject.

BACKGROUND

Cannabinoids are a class of chemical compounds found in the Cannabis plant. The two primary cannabinoids contained in Cannabis are cannabidiol, or CBD, and Δ9-tetrahydrocannabinol, or THC. CBD lacks the psychoactive effects of THC. Studies have shown that CBD can be used to treat disorders such as epilepsy, arthritis, and cancer.

FXS is the most common inherited intellectual disability in males and a significant cause of intellectual disability in females. It is caused by a mutation in the Fragile X Mental Retardation 1 (FMR1) gene located on the X chromosome and leads to dysregulation of the endocannabinoid system including reductions in endogenous cannabinoids (2-AG and anandamide [AEA]). The disorder negatively affects synaptic function, plasticity and neuronal connections, and results in a spectrum of intellectual disabilities, social anxiety, and memory problems. In the US, there are about 71,000 patients suffering with FXS.

"Behavior problems are often the most significant concern reported by parents, and high levels of stress and depression and low levels of quality of life for parents are commonly associated with elevated problem behaviors in children." Wheeler A, Raspa M, Bann C, Bishop E, Hassl D, Sacco H, Bailey D B. 2014. Anxiety attention problems, hyperactivity, and the Aberrant Behavior Checklist in fragile X syndrome. Am J Med Genet Part A 164A:141-155, 141. "As a result, reduction in behavior problems is a primary focus of ongoing clinical trials testing the efficacy of new medications for FXS." Wheeler at pages 141-142.

The Anxiety, Depression, and Mood Scale (ADAMS) is an instrument that is used by clinicians, doctors, and researchers to assess the level of anxiety, depression and mood in patients with intellectual disabilities, including FXS. ADAMS consists of questions grouped into five subscales, including (i) general anxiety, (ii) social avoidance, (iii) compulsive behavior, (iv) manic/hyperactive behavior, and (v) depressed mood. Each question is answered by a clinician/doctor on a four-point scale ranging from 0 ("not a problem") to 3 ("severe problem"). In addition to subscale scores, the ADAMS yields a total score.

The original Aberrant Behavior Checklist (ABC) was "designed to assess behavioral concerns of adults within institutional settings." Wheeler at page 142. Since then, the original ABC has been adapted to address patients who are not institutionalized and specifically to address FXS. Id. The Aberrant Behavior Checklist—FXS Specific (ABC-FXS) scale is used by clinicians, doctors, and researchers to access certain behaviors in patients with FXS. The ABC-FXS scale has six subscales including (i) irritability, (ii) hyperactivity, (iii) socially unresponsive/lethargic, (iv) social avoidance, (v) stereotypy, and (vi) in appropriate speech. Similar to ADAMS, the ABC-FXS scale is a four-point Likert-type scale ranging from 0 (not a problem) to 3 (problem is severe).

SUMMARY

The present disclosure relates to a method of treating one or more behavioral symptoms of Fragile X Syndrome in a subject. The method includes transdermally administering an effective amount of cannabidiol (CBD) to the subject wherein one or more behavioral symptoms of Fragile X Syndrome are treated in the subject.

In some embodiments, the CBD is (−)-CBD. The effective amount of CBD can be between about 50 mg to about 500 mg daily. In some embodiments, the effective amount of CBD is initiated at about 50 mg daily and titrated up to about 500 mg daily. The effective amount of CBD can be initiated at about 50 mg daily and titrated up to about 250 mg daily. In some embodiments, the effective amount of CBD is initiated at 250 mg daily. The effective amount of CBD can be initiated at 500 mg daily. In some embodiments, the 500 mg daily dose is administered to patients that weigh greater than 35 kg. The CBD can be administered in a single daily dose or in two daily doses. In some embodiments, the effective amount of CBD can be 390 mg in divided daily doses.

The CBD can be formulated as a gel or an oil. In some embodiments, the CBD is formulated as a permeation-enhanced gel. The gel can contain between 1% (wt/wt) CBD to 7.5% (wt/wt) CBD. In some embodiments, the gel contains 4.2% (wt/wt) CBD. In some embodiments, the gel contains 7.5% (wt/wt) CBD.

In some embodiments, the transdermal preparation can be a cream, a salve or an ointment. The CBD can be delivered by a bandage, pad or patch.

Alleviating one or more behavioral symptoms of Fragile X Syndrome can include an improvement in a total score of an Anxiety, Depression and Mood Scale (ADAMS). In some embodiments, alleviating one or more behavioral symptoms of FXS can include improvement in one or more subscales of ADAMS. Alleviating one or more behavioral symptoms of Fragile X Syndrome can include improvement in one or more measures of an Aberrant Behavior Checklist for Fragile X (ABC-FXS).

In some embodiments, the one or more behavioral symptoms is selected from the group consisting of general anxiety, social avoidance, compulsive behavior, manic/hyperactive behavior, irritability, lethargy, stereotypy, and inappropriate speech. The behavioral symptom that is alleviated can be any one of general anxiety, social avoidance, compulsive behavior, manic/hyperactive behavior, irritability, lethargy, stereotypy, inappropriate speech, emotional functioning, psychosocial health, written communication, socialization, play and leisure, coping skills, internalizing behavior, externalizing behavior, tantrum/mood liability, hyperactivity/impulsivity, quality of life, or any combination thereof. In some embodiments, a single symptom is alleviated. In some embodiment, two, three, four, five, six, seven, eight, or nine symptoms are alleviated.

The CBD can be administered transdermally on the subject's upper arm and shoulder. In some embodiments, the CBD is administered transdermally on the subject's thigh or back.

The CBD can be synthetic CBD. The CBD can be purified CBD. The CBD can be botanically derived.

Transdermally administering an effective amount of cannabidiol (CBD) can reduce an intensity of at least one adverse event or side effect relative to orally administering CBD. The at least one adverse event or side effect can be a gastrointestinal (GI) adverse event. The at least one adverse event or side effect can be liver function. In some embodiments, the at least one adverse event is somnolence. In some embodiments, the frequency and intensity of somnolence is reduced as an adverse event.

In another aspect, a method is provided to treat one or more behavioral symptoms of an autism spectrum disorder (ASD) in a subject by transdermally administering an effective amount of CBD to the subject wherein the one or more behavioral symptoms of ASD are treated in the subject.

ASD is a behavioral diagnosis having a range of symptoms that are generally characterized by an impaired ability to communicate and interact socially with other people.

The one or more behavioral symptoms of ASD that can be treated include, for example, social avoidance, general anxiety, hyperactivity, depressed mood and compulsive behavior. Alleviating one or more behavioral symptoms of ASD can include an improvement in a total score of an Anxiety, Depression and Mood Scale (ADAMS). In some embodiments, alleviating one or more behavioral symptoms of ASD can include improvement in one or more subscales of ADAMS.

In some embodiments, the CBD is (−)-CBD. The effective amount of CBD can be between about 50 mg to about 500 mg daily. In some embodiments, the effective amount of CBD is initiated at about 50 mg daily and titrated up to about 500 mg daily. The effective amount of CBD can be initiated at about 50 mg daily and titrated up to about 250 mg daily. In some embodiments, the effective amount of CBD is initiated at 250 mg daily. The effective amount of CBD can be initiated at 500 mg daily. In some embodiments, the 500 mg daily dose is administered to patients that weigh greater than 35 kg. The CBD can be administered in a single daily dose or in two daily doses. In some embodiments, the effective amount of CBD can be 390 mg in divided daily doses.

The CBD can be formulated as a gel or an oil. In some embodiments, the CBD is formulated as a permeation-enhanced gel. The gel can contain between 1% (wt/wt) CBD to 7.5% (wt/wt) CBD. In some embodiments, the gel contains 4.2% (wt/wt) CBD. In some embodiments, the gel contains 7.5% (wt/wt) CBD.

In some embodiments, the transdermal preparation can be a cream, a salve or an ointment. The CBD can be delivered by a bandage, pad or patch.

Alleviating one or more behavioral symptoms of ASD can include an improvement in a total score of an Anxiety, Depression and Mood Scale (ADAMS). In some embodiments, alleviating one or more behavioral symptoms of ASD can include improvement in one or more subscales of ADAMS.

In some embodiments, the one or more behavioral symptoms is selected from the group consisting of general anxiety, social avoidance, compulsive behavior, manic/hyperactive behavior. The behavioral symptom that is alleviated can be any one of general anxiety, social avoidance, compulsive behavior, manic/hyperactive behavior, or any combination thereof. In some embodiments, a single symptom is alleviated. In some embodiment, two, three, or four behavioral symptoms are alleviated.

The CBD can be administered transdermally on the subject's upper arm and shoulder. In some embodiments, the CBD is administered transdermally on the subject's thigh or back.

The CBD can be synthetic CBD. The CBD can be purified CBD. The CBD can be botanically derived.

Transdermally administering an effective amount of cannabidiol (CBD) can reduce an intensity of at least one adverse event or side effect relative to orally administering CBD. The at least one adverse event or side effect can be a gastrointestinal (GI) adverse event. The at least one adverse even or side effect can be a liver function adverse event. In some embodiments, the at least one adverse event is somnolence. In some embodiments, the frequency and intensity of somnolence is reduced as an adverse event.

DETAILED DESCRIPTION

As used herein, the term "treating" or "treatment" refers to mitigating, improving, relieving, or alleviating at least one symptom (such as a behavioral symptom) of a condition, disease or disorder in a subject, such as a human, or the improvement of an ascertainable measurement associated with a condition, disease or disorder.

As used herein, the term "clinical efficacy" refers to the ability to produce a desired effect in humans as shown through a Food and Drug Administration (FDA), or any foreign counterparts, clinical trial.

As used herein, the term "cannabidiol" or "CBD" refers to cannabidiol; cannabidiol prodrugs; pharmaceutically acceptable derivatives of cannabidiol, including pharmaceutically acceptable salts of cannabidiol, cannabidiol prodrugs, and cannabidiol derivatives. CBD includes, 2-[3-methyl-6-(1-methylethenyl)-2-cyclohexen-1-yl]-5-pentyl-1,3-benzenediol as well as to pharmaceutically acceptable salts, solvates, metabolites (e.g., cutaneous metabolites), and metabolic precursors thereof. The synthesis of CBD is described, for example, in Petilka et al., Hely. Chim. Acta, 52:1102 (1969) and in Mechoulam et al., J. Am. Chem. Soc., 87:3273 (1965), which are hereby incorporated by reference.

As used herein, the term "transdermally administering" refers to contacting the CBD with the patient's or subject's skin under conditions effective for the CBD to penetrate the skin.

Fragile X Syndrome (FXS) is a genetic condition that causes intellectual disability, behavioral and learning challenges and various physical characteristics. FXS affects 1 in 4,000 males and 1 in 8,000 females. Patients with FXS can exhibit one or more characteristics of ASD.

The present disclosure relates to a method of treating one or more behavioral symptoms of Fragile X Syndrome in a subject by transdermally administering an effective amount of cannabidiol (CBD) to the subject wherein one or more behavioral symptoms of Fragile X Syndrome are treated in the subject.

Clinical and preclinical data support the potential for CBD in treating epilepsy, arthritis, cancer, and Fragile X Syndrome. Therapeutic medicines have been developed that utilize innovative transdermal technologies to allow for sustained and controlled delivery of therapeutic levels of CBD. Transdermal delivery of cannabinoids (e.g., CBD) has benefits over oral dosing because it allows the drug to be absorbed through the skin directly into the bloodstream. This avoids first-pass liver metabolism, potentially enabling lower dosage levels of active pharmaceutical ingredients with a higher bioavailability and improved safety profile. Transdermal delivery also avoids the gastrointestinal tract, lessening the opportunity for GI related adverse events and the potential degradation of CBD by gastric acid into THC, which can be associated with unwanted psychoactive effects. Moreover, transdermal delivery of CBD reduces the intensity and frequency of somnolence adverse events, which are typically present in oral dosing of CBD. Transdermal delivery of CBD can avoid liver function adverse events, which are typically present in oral dosing of CBD. In some embodiments, transdermally administering an effective amount of CBD reduces an intensity of at least one adverse event by about 15% to about 95% relative to orally administering CBD.

The CBD can be in a gel form and can be pharmaceutically-produced as a clear, permeation-enhanced gel that is designed to provide controlled drug delivery transdermally with once- or twice-daily dosing. The CBD gel can between 1% (wt/wt) CBD to 7.5% (wt/wt) CBD. The CBD gel can have, for example, 4.2% (wt/wt) CBD or 7.5% (wt/wt) CBD). The CBD gel can be applied topically by the patient or caregiver to the patient's upper arm and shoulder, back, thigh, or any combination thereof.

The CBD gel can include diluents and carriers as well as other conventional excipients, such as wetting agents, preservatives, and suspending and dispersing agents.

The CBD gel can include a solubilizing agent, a permeation enhancer, a solubilizer, antioxidant, bulking agent, thickening agent, and/or a pH modifier. The composition of the CBD gel can be, for example, a. cannabidiol present in an amount of about 0.1% to about 20% (wt/wt) of the composition; b. a lower alcohol having between 1 and 6 carbon atoms present in an amount of about 15% to about 95% (wt/wt) of the composition; c. a first penetration enhancer present in an amount of about 0.1% to about 20% (wt/wt) of the composition; and d. water in a quantity sufficient for the composition to total 100% (wt/wt). Other formulations of the CBD gel can be found in International Publication No. WO 2010/127033, the entire contents of which are incorporated herein by reference.

EXAMPLES

Example 1: Study Design and Data

A total of 20 patients (mean age=10.8, SD=4.0) were enrolled in a 12-week study. Eighteen patients (14 males, 4 females) aged 6 to 17 years of age (mean=11.2 SD=3.96) with Fragile X as confirmed by molecular documentation of FMR1 full mutation completed the open label FAB-C study through week 12. CBD gel was added on to other medications being administered. The first six weeks of the study were designed to titrate dosing in patients. Dosing was initiated at 50 mg CBD daily and could be increased to 250 mg CBD daily. Weeks 7 through 12 of the study comprised the maintenance period where patients were treated at the dose established by week six at a maximum of 250 mg CBD daily. At the completion of the study, patients could enter an open label extension study for up to 12 months.

The primary endpoint for the trial was the change in the total score of the Anxiety, Depression, and Mood Scale (ADAMS) from baseline to week 12. The ADAMS is a 28-item scale designed to assess general anxiety, social avoidance, compulsive behavior, manic/hyperactive behavior, and depressed mood. It has been validated in patients with FXS.

Results for the primary endpoint are summarized in Table 1, detailing efficacy scales mean (standard deviation) values at baseline and week 12 for the ADAMS Total Score.

TABLE 1

|  | Baseline (n = 18) | Week 12 (n = 18) | Percent Change from Baseline (%; n = 18) | p Value* |
|---|---|---|---|---|
| ADAMS: Total Score | 32.1 (14.36) | 18.1 (8.32) | −43.61 | P < 0.0001 |

*P-values are presented for the comparison of the Week 12 value to the Baseline value for the total score and each subscale, among those who completed the study (n = 18).

The subscales of the ADAMS are summarized in Table 2, detailing efficacy scales mean (standard deviation) values at baseline and week 12.

TABLE 2

|  | Baseline (n = 18) | Week 12 (n = 18) | Percent Change from Baseline (%; n = 18) | p Value* |
|---|---|---|---|---|
| ADAMS: Manic/Hyperactive Behavior Subscale | 8.8 (3.99) | 6.1 (3.29) | −30.68 | p = 0.0003 |
| ADAMS: Depressed Mood Subscale | 2.9 (3.94) | 2.0 (2.35) | −31.03 | p = 0.1417 |
| ADAMS: Social Avoidance Subscale | 9.9 (5.18) | 4.8 (2.07) | −51.52 | p = 0.0002 |
| ADAMS: General Anxiety Subscale | 9.4 (4.35) | 4.6 (3.35) | −51.06 | P < 0.0001 |
| ADAMS: Compulsive Behavior Subscale | 2.7 (2.40) | 1.4 (1.42) | −48.15 | p = 0.0262 |

*P-values are presented for the comparison of the Week 12 value to the Baseline value for the total score and each subscale, among those who completed the study (n = 18).

Compared to the baseline total score, the CBD transdermal gel treated patients has a 44% reduction (p<0.0001) in the ADAMS Total Score. Furthermore, the CBD transdermal gel treated patients has statistically and clinically significant improvement compared to baseline in all but one of the ADAMS subscales (i.e., manic/hyperactive behavior, social avoidance, general anxiety, and compulsive behavior) at week 12. A significant change was not observed for the depressed mood subscale of the ADAMS.

Multiple secondary efficacy endpoints including the Aberrant Behavior Checklist—FXS Specific (ABC-FXS), the Pediatric Anxiety Rating Scale (PARS-R), Visual Analog Scale (VAS) for Anxiety, Hyperactivity and Tantrum/Mood Lability, the Vineland Adaptive Behavior (VLD) III, and the Pediatric Quality of Life (PedsQL™). Both the PARS-R and the Vineland scales are clinician-rated, while the other scales are caregiver-rated.

The primary and secondary endpoints were evaluated prior to and following 12 weeks of drug administration. The results of the secondary endpoints reinforce the results demonstrated in the ADAMS. Consistent with findings from the ADAMS, patients taking the CBD transdermal gel demonstrated statistically and clinically significant 12-week reductions in all subscales of the ABC-FXS (i.e., irritability, hyperactivity, socially unresponsive/lethargic, social avoidance, stereotypy, and inappropriate speech), and both total score calculations of the PARS-R (i.e., 5- and 7-item).

Patients also showed significant improvement between Baseline and Week 12 scores for all remaining scales except for the Physical Function, School Functioning, and Social Functioning subscales of the PedsQL, as well as some subscales of the VLD (e.g., communication, daily living skills). Both the VLD and ADAMS are being administered in the extension Phase 2 of the trial.

Results from the ABC-FXS are summarized in Table 3, detailing efficacy scales mean (standard deviation) values at baseline and week 12.

TABLE 3

|  | Baseline (n = 18) | Week 12 (n = 18) | Percent Change from Baseline (%; n = 18) | p Value* |
|---|---|---|---|---|
| ABC: Irritability | 17.7 (12.68) | 10.6 (11.03) | −40.11 | p = 0.0096 |
| ABC: Hyperactivity | 13.7 (9.09) | 9.8 (7.38) | −28.47 | p = 0.0237 |
| ABC: Socially Unresponsive/ Lethargic | 9.2 (6.40) | 4.1 (4.09) | −55.43 | p = 0.0034 |
| ABC: Social Avoidance | 5.1 (3.46) | 2.3 (2.22) | −54.90 | p = 0.0005 |
| ABC: Stereotypy | 8.1 (5.91) | 3.2 (3.07) | −60.49 | p = 0.0006 |
| ABC: Inappropriate Speech | 5.9 (2.30) | 3.5 (2.66) | −40.68 | p = 0.0018 |

*P-values are presented for the comparison of the Week 12 value to the Baseline, among those who completed the study (n = 18).

Results from the PARS-R are summarized in Table 4, detailing efficacy scales mean (standard deviation) values at baseline and week 12.

TABLE 4

|  | Baseline (n = 18) | Week 12 (n = 18) | Percent Change from Baseline (%; n = 18) | p Value* |
|---|---|---|---|---|
| PARS-R - 5 Item | 15.7 (3.88) | 10.6 (3.43) | −32.48 | p = 0.0006 |
| PARS-R - 7 Item | 21.3 (5.55) | 14.4 (4.54) | −32.39 | p = 0.0004 |

*P-values are presented for the comparison of the Week 12 value to the Baseline value, among those who completed the study (n = 18).

Results from the VAS for Anxiety, Hyperactivity and Tantrum/Mood Lability are summarized in Table 5.

TABLE 5

|  | Baseline (n = 18) | Week 12 (n = 18) | Percent Change from Baseline (%; n = 18) | p Value* |
|---|---|---|---|---|
| VAS - Hyperactivity/ Impulsivity | 5.9 (2.43) | 3.6 (2.49) | −38.98 | p = 0.0002 |
| VAS - Tantrum/ Mood Liability | 4.7 (2.09) | 3.2 (2.18) | −31.91 | p = 0.0023 |
| VAS - Anxiety | 6.0 (2.05) | 3.8 (1.93) | −36.67 | p = 0.0005 |

*P-values are presented for the comparison of the Week 12 value to the Baseline value, among those who completed the study (n = 18).

Results from the PedsQL are summarized in Table 6, detailing efficacy scales mean (standard deviation) values at baseline and week 12.

TABLE 6

|  | Baseline (n = 18) | Week 12 (n = 18) | Percent Change from Baseline (%; n = 18) | p Value* |
|---|---|---|---|---|
| PedsQL: Total Score | 57.8 (18.78) | 67.7 (18.27) | 17.13 | p = 0.0100 |
| PedsQL: Physical Functioning | 67.9 (27.36) | 78.0 (22.39) | 14.87 | p = 0.0606 |
| PedsQL: Emotional Functioning | 64.0 (20.72) | 78.3 (16.63) | 22.34 | p = 0.0394 |
| PedsQL: Social Functioning | 37.3 (24.70) | 49.0 (24.35) | 31.37 | p = 0.0717 |
| PedsQL: School Functioning | 55.7 (19.17) | 59.1 (22.47) | 6.10 | p = 0.3580 |
| PedsQL: Psycho-social Health | 52.4 (17.22) | 62.2 (18.91) | 18.70 | p = 0.0408 |

*P-values are presented for the comparison of the Week 12 value to the Baseline value, among those who completed the study (n = 18).

Results from the VLD III are summarized in Table 7, detailing efficacy scales mean (standard deviation) values at baseline and week 12.

TABLE 7

|  | Baseline (n = 18) | Week 12 (n = 18) | Percent Change from Baseline (%; n = 18) | p Value* |
|---|---|---|---|---|
| VLD III: Overall Adaptive Behavior Composite | 46.1 (16.29) | 48.9 (16.49) | 6.07 | p = 0.0472 |
| VLD III: Communication | 36.7 (18.52) | 39.2 (20.34) | 6.81 | p = 0.2968 |
| VLD III: Communication - Receptive | 3.9 (3.43) | 5.3 (4.34) | 35.90 | p = 0.0752 |
| VLD III: Communication - Expressive | 3.3 (3.63) | 3.7 (4.07) | 12.12 | p = 0.5070 |
| VLD III: Communication - Written | 4.4 (3.81) | 3.8 (3.64) | −13.64 | p = 0.0293 |
| VLD III: Daily Living Skills | 52.7 (21.19) | 54.6 (18.46) | 3.61 | p = 0.3911 |
| VLD III: Daily Living Skills - Personal | 5.7 (4.26) | 6.2 (4.33) | 8.77 | p = 0.3374 |

TABLE 7-continued

| | Baseline (n = 18) | Week 12 (n = 18) | Percent Change from Baseline (%; n = 18) | p Value* |
|---|---|---|---|---|
| VLD III: Daily Living Skills - Domestic | 9.6 (3.42) | 9.5 (3.09) | −1.04 | p = 0.9395 |
| VLD III: Daily Living Skills - Community | 4.6 (3.09) | 4.7 (2.93) | 2.17 | p = 0.5636 |
| VLD III: Socialization | 45.9 (16.22) | 50.9 (17.83) | 10.89 | p = 0.0344 |
| VLD III: Socialization - Interpersonal Relationships | 5.3 (3.51) | 5.9 (3.64) | 11.32 | p = 0.2937 |
| VLD III: Socialization - Play and Leisure | 3.4 (2.91) | 4.5 (3.93) | 32.35 | p = 0.0350 |
| VLD III: Socialization - Coping Skills | 6.6 (2.93) | 7.8 (2.84) | 18.18 | p = 0.0246 |
| VLD III: Maladaptive Behavior - Internalizing | 19.9 (1.71) | 18.7 (1.79) | −6.03 | p = 0.0486 |
| VLD III: Maladaptive Behavior - Externalizing | 18.7 (2.42) | 17.2 (2.66) | −8.02 | p = 0.0090 |

*P-values are presented for the comparison of the Week 12 value to the Baseline value, among those who completed the study (n = 18).

Among the 18 patients who completed 12 weeks of treatment, average improvement in overall anxiety and depression (ADAMS Total Score) reached 44% (p<0.01), with particular benefit observed for the General Anxiety (51%; p<0.01) and Compulsive Behavior subscales (48%; p<0.05). Additionally, improvements as measured by $ABC_{Fxs}$ ranging from 28% (Hyperactivity subscale; p0<0.05) to 60% (Stereotypy subscale; p0<0.01) were observed in aberrant behavior, with the Social Avoidance (p<0.01) and Social Unresponsiveness/Lethargy subscales (p<0.01) each improving by 55% during the treatment period. Beyond individual symptoms, quality of life improved by 17% (p=0.01).

The trial successfully met its primary endpoint, achieving a 44% improvement (P<0.0001) in the total ADAMS score at week twelve compared to baseline. The trial also achieved clinically meaningful improvements in all measures of the ABC-FXS, which address the key symptoms of FXS including irritability, hyperactivity, social unresponsiveness, social avoidance, stereotypy, and inappropriate speech.

Following the 12-week open-label study, patients were allowed to roll into a 1-year open-label extension study. 72% (n=13) of the 18 patients who completed the initial 12-week study rolled into the extension. While the open-label extension is ongoing, some data have been collected through Week 38 (12 weeks in initial study and up to 6 months in the extension study). Results from the extension study demonstrate continued gains in the two measures collected (ADAMS and $ABC_{Fxs}$). Indeed, those who have completed a Week 38 visit (n=4) showed significant gains from screening in overall anxiety and depression, with participants experiencing an average improvement in the ADAMS total score of 74%. Similar improvement was observed for aberrant behavior, ranging from 75% (Irritability subscale) to 96% (Social Avoidance subscale) and 97% (Socially Unresponsiveness/Lethargy subscale) at Week 38.

The open-label extension continues to be ongoing and data has been collected through Week 51. The results are summarized in Table 8 ($ABC_{Fxs}$) and Table (ADAMS).

TABLE 8

| | ($ABC_{FXS}$) | | | | |
|---|---|---|---|---|---|
| | Screening (baseline score) N = 12 | Week 12 Mean Change (%) N = 12 | Week 38 Mean Change (%) N = 9 | Week 51 Mean Change (%) N = 9 | Week 51 P values |
| Irritability | 22.3 | 51.1 | 63.7 | 59.2 | 0.0007 |
| Hyperactivity | 16.6 | 36.7 | 48.2 | 40.4 | 0.0037 |
| Socially Unresponsive/ Lethargic | 10.8 | 65.7 | 83.3 | 72.2 | 0.0035 |
| Social Avoidance | 5.7 | 57.9 | 75.4 | 77.2 | 0.0013 |
| Stereotypy | 9.7 | 60.8 | 73.2 | 64.9 | 0.0012 |
| Inappropriate Speech | 6.2 | 56.5 | 66.1 | 56.5 | <0.0001 |

TABLE 9

(ADAMS)

|  | Screening (baseline score) N = 12 | Week 12 Mean Change (%) N = 12 | Week 38 Mean Change (%) N = 12 | Week 51 Mean Change (%) N = 12 | Week 51 P values |
| --- | --- | --- | --- | --- | --- |
| Manic/Hyperactivity | 8.8 | 34.1 | 53.4 | 45.5 | 0.0014 |
| Depressed Mood | 3.2 | 43.8 | 62.5 | 59.4 | 0.0032 |
| Social Avoidance | 9.9 | 52.5 | 61.6 | 55.6 | 0.0004 |
| General Anxiety | 9.8 | 55.1 | 58.2 | 58.2 | <0.0001 |
| Compulsive Behavior | 3.2 | 50.0 | 59.4 | 59.4 | 0.0213 |
| Total Score | 33.3 | 48.6 | 59.2 | 54.4 | <0.0001 |

CBD gel was well tolerated, with excellent skin tolerability. One patient discontinued due to worsening of pre-existing eczema. No other adverse events led to discontinuation and no adverse events were considered severe. The most common adverse events were mild-moderate gastroenteritis (n=6) and upper respiratory tract infection (n=5). However, no patient experienced drug-related GI events during the 12-week treatment period and no THC was detected in the plasma.

The clinical results of the trial are significant for the many patients worldwide with FXS who currently have no approved therapeutic options to treat their symptoms. The data, in particular the improvements in anxiety, social avoidance, and irritability as measured by ADAMS, ABC-FXS and PARS-R, are significant. The CBD gel was very well tolerated in children and adolescents with FXS.

Example 2: Patient Monograph as Reported by Parent

This is the report regarding a 7 year old child participating in the above study and continuing on an extension study—as reported by the caregiver. The caregiver's son has full mutation Fragile X Syndrome. He is reported, prior to the trial, to be non-verbal, severely intellectually impaired, visually impaired, still in need of diapers and as having very severe GI issues requiring that he is fed by a feeding tube every two hours. Prior to the beginning the trial the child never ever made eye contact, rarely could leave his home without severe emotional distress, did not initiate any form of communication at all, intensely disliked being touched including by his parents, would not allow even family to sit next to him, and would leave the room if anyone walked into it.

Within the first two weeks of the trial, the patient began to make more eye contact, initiated physical contact with his family, e.g., grabbing his mother's hand, initiated emotional contact with his family including seeking to be in the same room with his family, and exhibited improved ability to leave the house, even to the extent the family could take their very first vacation together.

After the end of the initial trial and a few weeks into the extended trial, the caregiver recorded another big change in the patient. He started greeting his family, initiated and engaged in games that are more complex, exhibited/shared preferences for things instead of only rejecting all choices, and he began acknowledging the family pets. He also allowed his doctor to touch him and hold onto him without getting distressed. Patient began to use body signing (sign language) for the very first time. Patient communicated very clearly that he missed his mother for the very first time and was eager to be embraced and held by his mother.

Patient is reported to be happier, more relaxed, able to engage the world in ways he could not before, and able to learn new skills that he could not previously. His teachers, therapists and aids have also remarked in the changes in the patient.

What is claimed is:

1. A method of treating a human suffering from an autism spectrum disorder comprising:
    transdermally administering via a gel or cream a therapeutically effective amount of purified cannabidiol to the human suffering from the autism spectrum disorder to effectively treat the autism spectrum disorder in the human in need thereof.

2. The method of claim 1, wherein the cannabidiol is (−)-cannabidiol.

3. The method of claim 1, wherein the therapeutically effective amount of cannabidiol is 250 mg total daily.

4. The method of claim 1, wherein the therapeutically effective amount of cannabidiol is 500 mg total daily.

5. The method of claim 1, wherein the cannabidiol is formulated as a permeation-enhanced gel.

6. The method of claim 1, wherein the cannabidiol is administered in a single-daily dose.

7. The method of claim 1, wherein the cannabidiol is administered in two daily doses.

8. The method of claim 1, wherein the therapeutically effective amount of cannabidiol is between about 50 mg to 500 mg total daily.

* * * * *